(12) United States Patent
Giasson et al.

(10) Patent No.: US 10,383,709 B2
(45) Date of Patent: Aug. 20, 2019

(54) DENTAL BAR

(71) Applicant: Nobel Biocare Services AG, Zurich-Flughafen (CH)

(72) Inventors: David Giasson, Quebec (CA); Alexandre Gilbert, Quebec (CA); Ion Dumitrescu, Quebec (CA); Myriam Manai, Quebec (CA); Adam Roberts, Edmond, OK (US)

(73) Assignee: Nobel Biocare Services AG, Zurich-Flughafen (CH)

( * ) Notice: Subject to any disclaimer, the term of this patent is extended or adjusted under 35 U.S.C. 154(b) by 0 days.

(21) Appl. No.: 13/799,691

(22) Filed: Mar. 13, 2013

(65) Prior Publication Data

US 2014/0106303 A1    Apr. 17, 2014

Related U.S. Application Data

(60) Provisional application No. 61/713,412, filed on Oct. 12, 2012.

(51) Int. Cl.
*A61C 8/00*    (2006.01)
*A61C 13/00*    (2006.01)
(Continued)

(52) U.S. Cl.
CPC .......... *A61C 8/0048* (2013.01); *A61C 8/0095* (2013.01); *A61C 13/0004* (2013.01); *G16H 20/40* (2018.01); *Y10T 29/49567* (2015.01)

(58) Field of Classification Search
CPC ..... A61C 8/0048; A61C 13/0004; A61C 5/10; Y10T 29/49567
(Continued)

(56) References Cited

U.S. PATENT DOCUMENTS 3,514,858 A     6/1970   Silverman
4,689,013 A *   8/1987   Lustig ..................... 433/181
                         (Continued)

FOREIGN PATENT DOCUMENTS

DE    20 2006 011 340    1/2007
EP        2 345 386 A1   7/2011
                (Continued)

OTHER PUBLICATIONS

Photos from a third party (Panthera) website downloaded Nov. 22, 2012.
(Continued)

*Primary Examiner* — Cris L. Rodriguez
*Assistant Examiner* — Hao D Mai
(74) *Attorney, Agent, or Firm* — Knobbe Martens Olson & Bear LLP

(57) ABSTRACT

An overdenture bar includes a U-shaped support beam configured to being coupled to a plurality of dental implants and extending generally above the mucus membrane of the gums. The U-shaped support beam has an anterior region and a pair of posterior extensions. At least one portion of the U-shaped support beam includes a plurality of retention elements extending generally normal to an outer surface of the U-shaped support beam in a plurality of directions. A method for producing a dental bar model on a CAD/CAM program to be fitted on a patient's upper or lower gingival surface includes the steps of selecting a longitudinal portion of the bar, adding protrusions to an upper portion of the bar and/or positioning a buccal finish line and a lingual finish between two boundary lines. The boundary lines illustrate the highest and lowest position of the finish lines.

23 Claims, 8 Drawing Sheets

(51) Int. Cl.
*A61C 5/10* (2006.01)
*G16H 20/40* (2018.01)

(58) Field of Classification Search
USPC .......................................... 433/167, 172–176
See application file for complete search history.

(56) References Cited

U.S. PATENT DOCUMENTS

| | | | |
|---|---|---|---|
| 4,741,698 | A | 5/1988 | Andrews |
| 4,767,328 | A | 8/1988 | Branemark |
| 4,931,016 | A | 6/1990 | Sillard |
| 4,932,016 | A | 6/1990 | Yoshida et al. |
| 5,052,928 | A | 10/1991 | Andersson |
| 5,234,341 | A | 8/1993 | Johansen |
| 5,419,700 | A | 5/1995 | Sillard |
| 5,427,906 | A | 6/1995 | Hansen |
| 5,429,505 | A | 7/1995 | Fortin |
| 5,460,526 | A | 10/1995 | Bosker |
| 5,675,070 | A | 10/1997 | Gelperin |
| 5,716,214 | A | 2/1998 | Lund et al. |
| 5,725,376 | A | 3/1998 | Poirier |
| 6,250,924 | B1 | 6/2001 | Luotio |
| 6,305,938 | B1 | 10/2001 | Branemark |
| 6,322,364 | B1 | 11/2001 | Oshida et al. |
| 6,382,975 | B1 | 5/2002 | Poirier |
| 6,413,660 | B1 | 7/2002 | Daskalon et al. |
| 6,527,553 | B2 | 3/2003 | Yeung |
| 6,607,386 | B1 | 8/2003 | Andersson et al. |
| 6,666,684 | B1 * | 12/2003 | Names ..................... 433/173 |
| 6,814,575 | B2 | 11/2004 | Poirier |
| 6,902,401 | B2 | 6/2005 | Jorneus et al. |
| 6,915,178 | B2 | 7/2005 | O'Brien et al. |
| 7,175,435 | B2 | 2/2007 | Andersson et al. |
| 7,214,061 | B2 | 5/2007 | Fortin |
| 7,234,940 | B2 | 6/2007 | Weissman |
| 7,279,054 | B2 | 10/2007 | Cascone |
| 7,331,789 | B2 | 2/2008 | Karmaker et al. |
| 7,463,942 | B2 | 12/2008 | O'Brien et al. |
| 7,747,418 | B2 | 6/2010 | Leu et al. |
| 7,806,691 | B2 | 10/2010 | Berger |
| 8,457,772 | B2 * | 6/2013 | Giasson ............. A61C 13/0004 433/167 |
| 8,892,235 | B2 * | 11/2014 | Choi ....................... A61C 1/084 433/201.1 |
| 2003/0183964 | A1 | 10/2003 | Daskalon et al. |
| 2003/0211444 | A1 * | 11/2003 | Andrews ...................... 433/172 |
| 2004/0120781 | A1 | 6/2004 | Luca et al. |
| 2004/0197737 | A1 | 10/2004 | Uckelmann et al. |
| 2005/0123879 | A1 | 6/2005 | Andersson et al. |
| 2005/0142517 | A1 | 6/2005 | Frysh et al. |
| 2005/0221258 | A1 | 10/2005 | Hall |
| 2005/0266382 | A1 | 12/2005 | Soler et al. |
| 2006/0105294 | A1 * | 5/2006 | Burger et al. ................. 433/167 |
| 2006/0223029 | A1 * | 10/2006 | Berger .......................... 433/172 |
| 2007/0082321 | A1 | 4/2007 | Uckelmann et al. |
| 2007/0190490 | A1 | 8/2007 | Giorno |
| 2007/0264612 | A1 | 11/2007 | Mount |
| 2008/0020343 | A1 | 1/2008 | Mount |
| 2008/0050700 | A1 | 2/2008 | Weber et al. |
| 2008/0090208 | A1 | 4/2008 | Rubbert |
| 2008/0138758 | A1 | 6/2008 | Fricke |
| 2008/0241798 | A1 | 10/2008 | Holzner et al. |
| 2008/0248441 | A1 | 10/2008 | Clerck |
| 2008/0286718 | A1 * | 11/2008 | Franke et al. .................. 433/49 |
| 2009/0004626 | A1 * | 1/2009 | Goldman ...................... 433/174 |
| 2009/0248184 | A1 * | 10/2009 | Steingart ................ A61C 1/082 700/98 |
| 2009/0325125 | A1 | 12/2009 | DiAngelo |
| 2012/0058449 | A1 | 3/2012 | Sklarski et al. |
| 2012/0088208 | A1 | 4/2012 | Schulter et al. |
| 2012/0094253 | A1 | 4/2012 | Berger |
| 2012/0179281 | A1 * | 7/2012 | Steingart ............ A61C 13/0004 700/97 |
| 2013/0216974 | A1 * | 8/2013 | Schmalzle et al. ............. 433/75 |
| 2014/0162211 | A1 | 6/2014 | Mullaly et al. |
| 2014/0178839 | A1 * | 6/2014 | Berger ............... A61C 13/2255 433/173 |
| 2015/0238290 | A1 * | 8/2015 | Wouters ............. A61C 13/0004 700/98 |

FOREIGN PATENT DOCUMENTS

| | | | |
|---|---|---|---|
| WO | WO 2006/103648 A1 | 10/2006 | |
| WO | WO 2010139031 A2 * | 12/2010 | ............... A61C 8/00 |
| WO | WO 2012/041329 | 4/2012 | |

OTHER PUBLICATIONS

Letter dated Aug. 12, 2014 from Brian E. Ainsworth including Attachment 1 (partially redacted) and Attachment 2.
Affidavit of Martin Robillard dated Mar. 7, 2013.
Screenshots obtained in Oct. 2012 from a third party (Panthera) website.
Screenshots from a third party (Panthera) website dated Apr. 2, 2012.

* cited by examiner

DENTAL BAR

CROSS-REFERENCE TO RELATED APPLICATIONS

This application claims the benefit of priority under 35 U.S.C. § 119(e) of U.S. Provisional Application No. 61/713,412, filed on Oct. 12, 2012, the entirety of which is incorporated herein by reference.

BACKGROUND OF THE INVENTION

1. Field of the Invention

The present application relates to a dental bar and a method of designing a dental bar and, more particularly, to an overdenture bar design and a computer-aided process of designing an overdenture bar.

2. Description of the Related Art

An overdenture bar or dental bar can be an important part the implant-based dental restorations for partially dentate, edentulous or fully edentulous patients. Implant-based dental restorations can have many advantages over standard removable dental restorations since the dental implants can enable the patient to get firmer bites. An important step in the dental restoration process is the fabrication of the overdenture or dental bar. The overdenture bar is supported on the installed dental implants in the patient and also supports the denture. The denture can be removable or permanently attached (e.g., polymerized) to the overdenture bar. In this manner, the overdenture bar structurally supports the denture on the installed dental implants.

In the past, overdenture bars were manually designed by a dental technician. This process was a lengthy and labor intensive process. Today, there exist techniques for generating patient-specific or custom overdenture bars. The NobelProcera™ Implant Bar Overdenture system, for example, involves a computer-aided design ("CAD") and/or a computer-aided manufacturing ("CAM") process in which the individualized overdenture bars are custom made to fit implants previously installed in a patient. In such a system, a dentist can take an impression of a patient's mouth using conventional procedures. In this manner, the position and orientation of the existing dental implants in a patient's mouth can be recorded. A dental laboratory then fabricates a model of the patient's mouth from the impression and can fabricate devices to record the maxillo-mandibular relationship. The dentist can verify and record the maxillo-mandibular relationship using conventional procedures. The dental laboratory then fabricates a wax setup and sends it to the dentist for a trial fitting in the patient to ensure correct function, esthetics and phonetics. The model and wax setup can then be scanned in using a scanner (e.g., a NobelProcera Scanner). Using a CAD/CAM system (e.g., NobelProcera Software), the dental laboratory can design a wide variety of implant bars on many different implant systems. The CAD data of the overdenture bar can be sent to a manufacturing center, where via computer-aided manufacturing, the overdenture bar is created (e.g., through precision milling). The overdenture bar can then be shipped to the dental laboratory along with clinical screws, and if desired, additional attachments. The laboratory can finalize the restoration and position the restoration on the overdenture bar and send the restoration and the overdenture bar to the dentist for installation.

While such techniques have proven to be advantageous and useful, there is a general desire to continue to improve the design of such overdenture bars.

SUMMARY

Accordingly, disclosed herein is an overdenture bar and methods of producing an overdenture bar using CAD/CAM processing.

In accordance with one embodiment, an overdenture bar comprises a U-shaped support beam configured to being coupled to a plurality of dental implants and extending generally above the mucus membrane. The U-shaped support beam can include an anterior region and a pair of posterior portions. At least one portion of the U-shaped support beam includes a plurality of retention elements extending generally normal to an outer surface of the U-shaped support beam in a plurality of directions.

In accordance with one embodiment, an overdenture bar comprises a U-shaped support beam configured to being attached to a plurality of dental implants and extending generally above the mucus membrane. The U-shaped support beam can include an anterior region and a pair of posterior extensions. The U-shaped support beam can have a cross-sectional profile in which the posterior extensions are wider than the anterior region.

In accordance with one embodiment, an overdenture bar comprises a U-shaped support beam configured to being attached to a plurality of dental implants and extending generally above the mucus membrane. The U-shaped support beam includes an anterior region and a pair of posterior extensions. The U-shaped support beam includes a one or more protrusions extending from an upper surface of the U-shaped bar. In one arrangement, the bar includes a denture comprising a plurality of replacement teeth and the one or more protrusions are aligned with at least some of the plurality of teeth.

In further arrangements, the overdenture bar described above can include a denture having denture material wrapped around at least a portion of the overdenture bar.

In accordance with one embodiment, a method for producing a dental bar model to be fitted on a patient's upper or lower gingival surface is provided. The method comprises selecting a longitudinal portion of the bar; and modifying the cross-sectional profile of the bar. In one further arrangement, the step of modifying the cross-sectional profile of the bar includes modifying an anterior region of the bar. In another arrangement, modifying the anterior region of the bar includes making a cross-section of the anterior region thinner than a portion of the posterior extensions of the bar.

In accordance with one embodiment, a method for producing a dental bar model to be fitted on a patient's upper or lower gingival surface is provided. The method comprises a design phase in which the following steps are performed: selecting a longitudinal portion of the bar, and adding protrusions to an upper portion of the bar. In one further arrangement, the design phase of the bar includes the step of positioning one or more finish lines. In one further arrangement, the design phase of the bar includes a menu option for providing a buccal finish line and a lingual finish line, preferably between two boundary lines, wherein said boundary lines illustrate the highest and lowest position of the finish lines.

In accordance with one embodiment, a method for producing a dental bar model to be fitted on a patient's upper or lower gingival surface is provided. The method comprises design phase in which the following steps are performed:

selecting an area on a surface of the bar, and adding retention elements to the surface of the bar. In one further arrangement, the design phase of the bar includes the step of adding multiple retention elements to the surface of the bar. In one further arrangement, the design phase of the bar includes a menu option for specifying a dimension of the retention element.

In further arrangements, the methods described above can also include adding a wrap around denture to the bar.

DETAILED DESCRIPTION OF THE EMBODIMENTS

Embodiments of the invention will now be described with reference to the accompanying figures, wherein like numerals refer to like elements throughout. Although several embodiments, examples and illustrations are disclosed below, it will be understood by those of ordinary skill in the art that the invention described herein extends beyond the specifically disclosed embodiments, examples and illustrations, and can include other uses of the invention and obvious modifications and equivalents thereof. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

As will be described, the present application relates to an overdenture or dental bar and a method of designing an overdenture or dental bar and, more particularly, to an improved structure for an overdenture bar design and a computer-aided process of designing such an overdenture or dental bar. It should be appreciated that while the figures and description herein often refer to an overdenture bar, which are particularly useful for treating fully edentulous patients, in modified embodiments, the overdenture or dental bar can be configured to treat patients that are not fully edentulous (e.g., partially edentulous).

Figure 1:
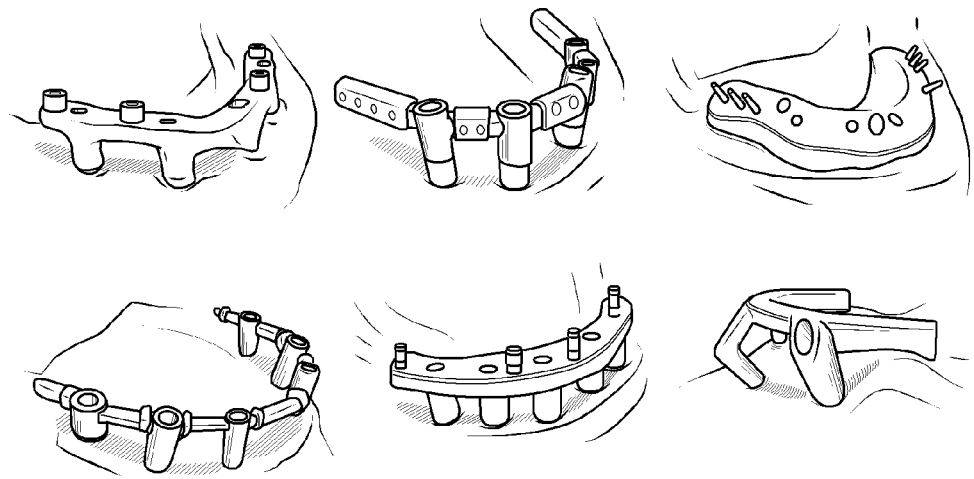
FIG. 1 illustrates embodiments of prior art overdenture bars.

FIG. 1 illustrates several embodiments of prior art overdenture bars. As described in the background section, an overdenture bar or dental bar can be an important part of implant-based dental restorations for partially or fully edentulous patients. The overdenture bar can be supported on installed dental implants in the patient. The overdenture bar can also support the denture, which can be removable or permanently attached to the overdenture bar. In this manner, the overdenture bar structurally supports a denture on the installed dental implants. As shown in FIG. 1, overdenture bars are often "U-shaped" with a front, or anterior region, that corresponds to the curved section of a "U" shape, and two back, or posterior extensions, that correspond to the straight sections of a "U" shape. The overdenture bar additionally can often include various cylinders, posts, and/ or pegs that can be shaped and connected to the overdenture bar to the dental implant and denture.

Figure 2:
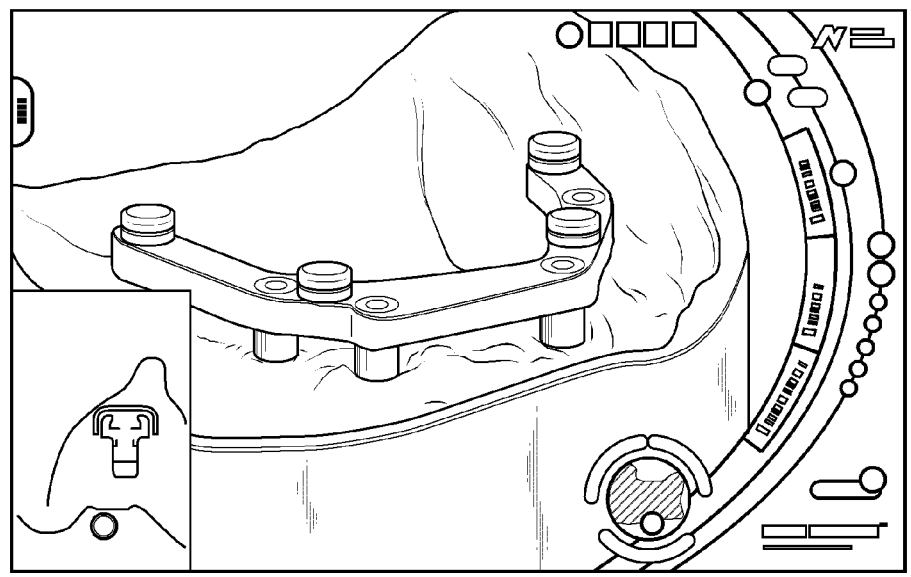
FIG. 2 illustrates a prior art CAD software program used to design an overdenture bar.

FIG. 2 illustrates a prior art CAD software program (NobelProcera™ Software), which is configured to allow a technician to custom design an overdenture bar. As described in the background section, a model and wax setup can be scanned into a CAD system such that a technician can view the position of the dental implants installed in the patient. In the system shown in FIG. 2, the user can then use the software to cut cylinders, position attachments, form the implant bar. The software allows the user to change views and to choose the type of implant bar and distal extensions. The software also allows the user to visualize the prosthetic setup to ensure an optimal bar design, such as vertical height, distance to soft tissue and attachment position. The software also allows the user to display only the desired elements, such as the model, prosthetic setup, overdenture bar or connectors. The software additionally allows the user to send the final bar design straight to the manufacturing facility.

FIGS. 3A-3D are schematic illustrates of embodiments of a dental bar 100 having certain features. As will be described below, the illustrated denture bar can be custom-made or free-formed using a software system, such as the NobelProcera™ Software, described above with reference to FIG. 2. In addition, in one embodiment, the dental bar can be configured to be used as a "wrap around" bar. In a "wrap around" bar, the denture material is wrapped around the upper and lower surfaces of the bar (i.e., the bar can be embedded, at least partially, in the denture material). The denture material can be acrylic, such as those sold under the brand names VitaVM, Lucitone, Palapress, Brenent etc. The denture material can additionally or alternatively be made out of materials such as a ceramic and/or polymeric composition. The dental bar can be made out of titanium or any other biocompatible material that can provide mechanical support.

The dental bar 100 of FIGS. 3A-D can have several features that can be used individually or in combination with each other. In one embodiment, for example, the dental bar can have two or more different design segments. In the illustrated arrangement of FIGS. 3A-D, the anterior region 110 (see the boxed section in FIG. 3A) can have a higher, taller and/or thinner profile as compared to the posterior extensions 120 (see boxed section of FIG. 3B). In this manner, the anterior region 110 can form a support flange 130. This arrangement can advantageously provide additional room for the denture material in the anterior section of the final prosthesis, which often has less anatomical space as compared to the posterior extensions of the final prosthesis. In addition, the higher, taller and/or thinner bar structure of the anterior region 110 can provide additional support for the dental material used in this section of the final prosthetic. Additionally, the overdenture bar 100 can include support posts 140 to connect and/or support the bar 100 to the dental implant and/or denture. In the illustrated embodiments of FIGS. 3A-D, the support posts 140 extend substantially vertically. However, in other embodiments, the support posts 140 can be angled and/or extend in different directions.

Figures 3A, 3B:
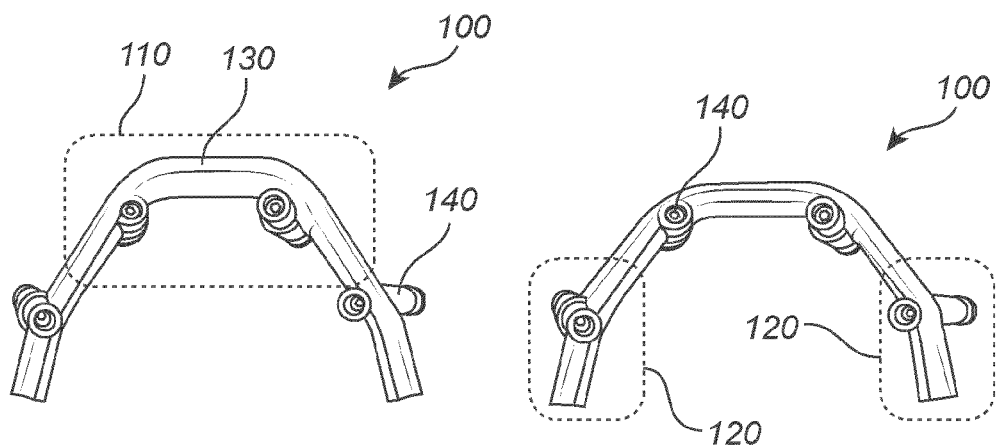
FIG. 3A illustrates a top view of an overdenture bar having certain features according to one embodiment.
FIG. 3B illustrates a top view of an overdenture bar having certain features according to one embodiment.
Figures 3C, 3D:
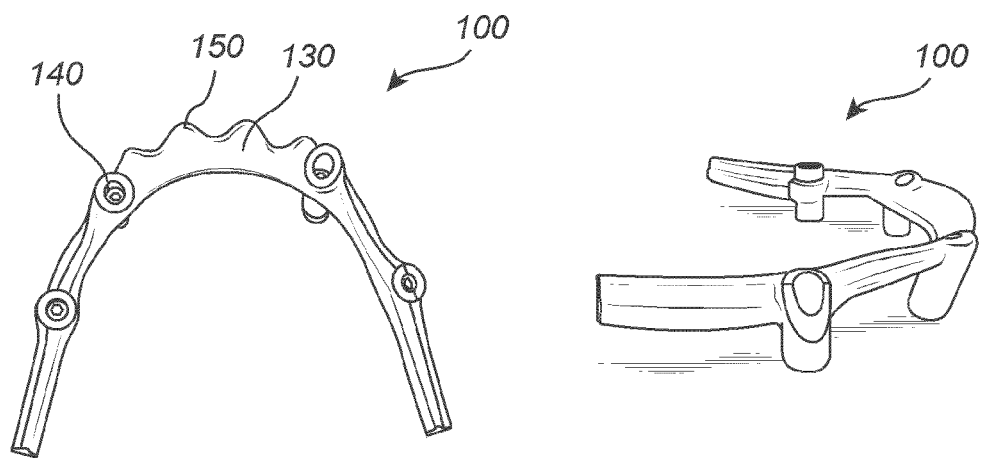
FIG. 3C illustrates a top view of an overdenture bar having certain features according to one embodiment.
FIG. 3D illustrates a side perspective view of an overdenture bar having certain features according to one embodiment.

In addition to, or as an alternative to, the features of FIGS. 3A and/or 3B, the anterior 110 and/or the posterior 120 extensions of the bar 100 can include one or more protrusions 150 (best depicted in FIG. 3C). In the embodiment illustrated in FIG. 3C, the protrusions 150 are finger-like and extend from the support flange 130 or upper part of the anterior region 110 of the bar 100. Such protrusions 150 can be configured to align generally with areas of the final restoration that correspond to tooth structures. In the illustrated arrangement in FIG. 3C, the protrusions 150 have a generally triangular shape with a rounded apex. In modified embodiments, the protrusions 150 can have different shapes (e.g., semi-circular and/or rectangular with rounded edges). In one embodiment, the protrusions 150 can extend in one or more different directions from the bar 100. In one embodiment, the protrusions 150 can extend in a substantially horizontal direction, a substantially vertical direction, or some orientation in between. In one embodiment, the protrusions 150 can extend in tangential, orthogonal, and/or askew directions. It should be appreciated that some or all of the protrusions 150 can extend in different directions relative to each other. An advantage of such protrusions 150 is that they can provide the bar 100 with additional lateral support for the tooth structures of the final dental restoration. FIG. 3D illustrates a side perspective embodiment of a bar 100 showing the features depicted in FIGS. 3A and 3B. In the schematic illustrates of FIGS. 3A-3D, the protrusions 150 can be included on any of the illustrated embodiments (e.g., the embodiments of FIGS. 3A, 3B and 3D). In addition, the schematic illustrations of FIGS. 3A-3D, the retention elements 180 (described below) can be included on any of the illustrated embodiments of FIGS. 3A-3D in addition to the protrusions 150 or without protrusions 150.

In one embodiment, the CAD software can provide a handle line positioned at or near the crest of the support flange 130. The CAD user can then manipulate the handle line to shape the upper edge of the support flange 130 to form the protrusions 150. In one arrangement, an image of a wax build up of the denture can be superimposed on the image of the bar 100 such that user can align the protrusions 150 with the tooth structures.

With continued reference to FIGS. 3A-D, as noted above, the bar 100 can be provided with different design geometries within the bar 100. In one arrangement, the CAD software program is configured such that the user can select different design geometries by placing a position maker on the bar 100 to separate the anterior region 110 from the posterior extensions 120 of the bar. For example, in the illustrated arrangement in FIGS. 3A and 3B, a box can be drawn around the selected portions. Preferably, such divisions do not need to be based on the support posts 140 but can extend between the support posts 140. The CAD software preferably also provides the ability for the user to adapt and create the protrusions 150 in the upper part of the bar 100 both in the anterior 110 and/or posterior 120 extensions. For example, in one embodiment, a portion of the bar can be clicked on (e.g., with input devices such as a keyboard, mouse or stylus) in the CAD environment and dragged upward to create the protrusion.

Figure 4A:
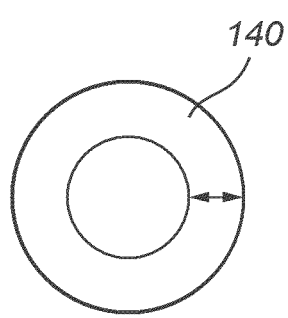
FIG. 4A illustrates a cross-sectional view of the support posts of an overdenture bar according to one embodiment.
Figure 4B:
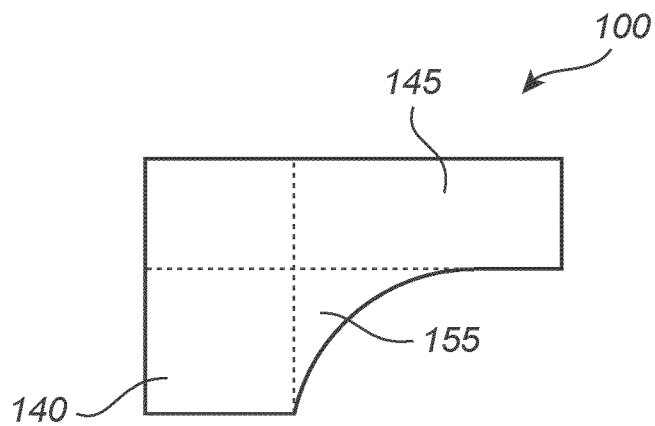
FIG. 4B illustrates a design feature in an overdenture bar according to one embodiment.

With reference to FIGS. 4A, 4B, 5A and 5B, in one embodiment that can be used in combination or as an alternative to the other embodiments described herein, the CAD program gives the user the ability to customize one or more of the following features of the overdenture bar. FIG. 4A illustrates a cross-sectional view of the support posts 140 of an overdenture bar 100 according to one embodiment. With reference to FIG. 4A, the user can adjust the size and wall thickness of the support posts 140 to a customized dimension. In one embodiment, the support posts 140 are preferably 2 mm in wall thickness. FIG. 4B illustrates a design feature in an overdenture bar 100 according to one embodiment. FIG. 4B depicts the connection between the support posts 140 and the support beams 145 of the overdenture bar 100. As illustrated in FIG. 4B, the connection can include a bulk portion 155, such as a fillet or chamfer, to add strength to the overdenture bar 100. In one embodiment, the connection can be 4 mm×6 mm.

Figure 5A:
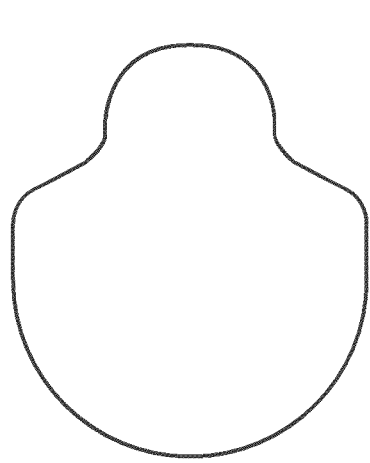
FIG. 5A illustrates a cross-sectional view of an overdenture bar according to one embodiment.
Figure 5B:
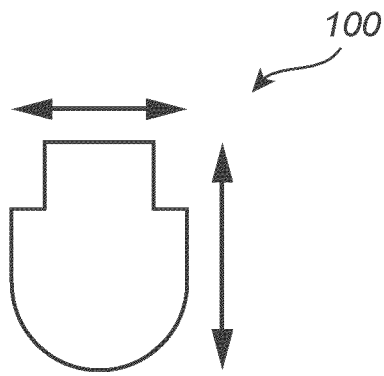
FIG. 5B illustrates a cross-sectional view of an overdenture bar according to one embodiment.

FIGS. 5A and 5B illustrate cross-sectional views of overdenture bars 100 according to certain embodiments. With reference to FIGS. 5A and 5B, the user can adjust the cross-section of the posterior extensions 120 of the bar 100 to have a different cross-section than the anterior region 110 of the bar 100, for example to provide for stronger designs. In one embodiment, the cross-section of the bar can be 4 mm by 4 mm. Additionally, the user can individually adjust the radii of the buccal edges (the side of the bar adjacent the inside of the cheek) and lingual edges (the side of the bar adjacent the tongue) for both the anterior 110 and/or posterior 120 extensions of the bar 100. With further reference to FIGS. 5A and 5B, the user can adjust the shape of the bottom of the cross-section of the bar 100 (i.e., the portion facing tissue) to have individually controlled radii on the buccal and/or lingual sides of the bar 100. In the embodiments shown in FIGS. 5A and 5B, the bottom of the cross-section is shown with arced or curved edges on both the buccal and lingual sides of the bar 100. It should be appreciated that the type of cross-sectional shape and/or the presence and size of radii can be varied. In one embodiment, the radii of the buccal and/or lingual sides of the bar can be controllable through a parameter in the CAD program. In addition, the CAD software preferably also includes tools for the custom design of any segment of the bar such that the height, width and/or contour of the base and/or upper sections are fully controllable.

Figure 6:
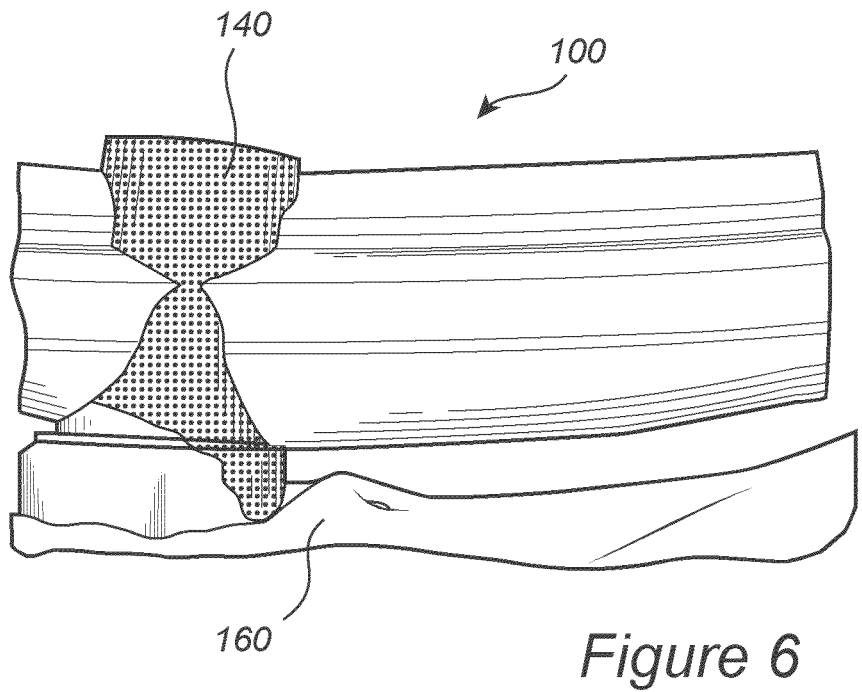
FIG. 6 illustrates a side view of a posterior end of an overdenture bar according to one embodiment.

FIG. 6 illustrates a side view of a posterior end of an overdenture bar 100 according to one embodiment. With reference to FIG. 6, the software CAD program can include, additionally or alternatively, a feature allowing the user to define the fit of the bar 100 and support posts 140 to the gums or tissue 160 and/or the distance to the gums 160. For example, in the illustrated embodiment, the user can set the distance the overdenture bar 100 lies above the gum line 160. In one embodiment, the distance between the bar 100 and the gums 160 can be approximately 1 mm.

Figure 7:
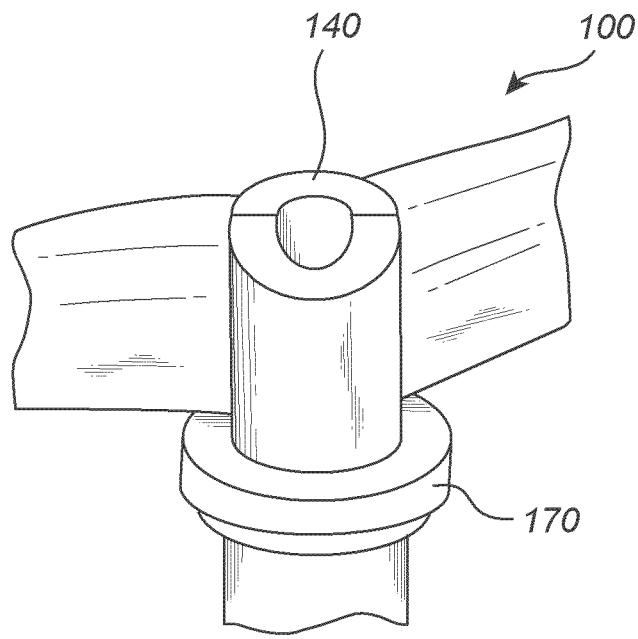
FIG. 7 illustrates a side perspective view of a support post of an overdenture bar according to one embodiment.

FIG. 7 illustrates a side perspective view of a support post 140 of an overdenture bar 100 according to one embodiment. With reference to FIG. 7, the software CAD program can include, additionally or alternatively, a feature allowing the user to custom control a support post collar 170 in height and/or diameter to allow for design of a acrylic finish line. For example, in one embodiment, both the inner collar 170 and/or outer collar 170 height and/or diameter can be selected. In one embodiment, a feature can also be provided to provide a bevel on the collar 170. In the illustrated embodiment in FIG. 7, the collar is shown substantially vertically. However, the collar can also be designed to be angled on a preferred axis or orientation.

Figure 8:
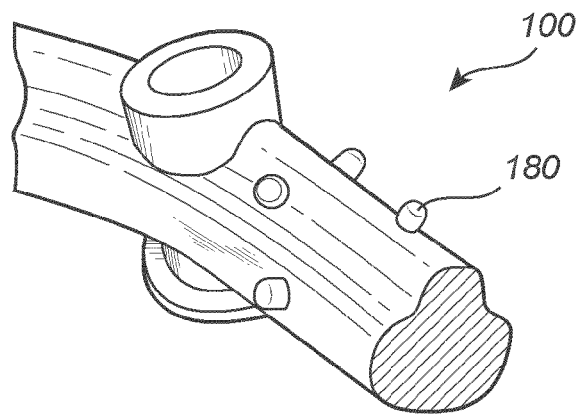
FIG. 8 illustrates a side perspective view of a posterior end of an overdenture bar according to one embodiment.

FIG. 8 illustrates a side perspective view of a posterior end of an overdenture bar 100 according to one embodiment. With reference to FIG. 8, the software CAD program can include, additionally or alternatively, a feature allowing the user to add retention elements 180 on the bar 100. In one embodiment, the retention elements 180 can be added directly onto the bar design to create retention for the material (e.g., acrylic) used to form the denture that is embedded around the bar 100. The retention elements 180 can take the form of pins, bumps, notches, hooks and/or protrusions or any other shape as is known to create retention. In one embodiment, the retention elements 180 can be placed manually by the user in the software CAD program.

Figure 9:
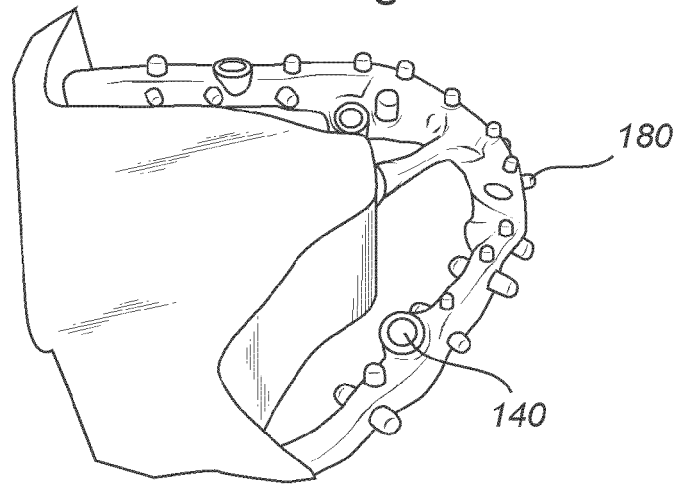
FIG. 9 illustrates a top perspective view of an overdenture bar according to one embodiment.

FIG. 9 illustrates a top perspective view of an overdenture bar 100 according to one embodiment. With reference to FIG. 9, in one embodiment, the overdenture bar 100, including the retention elements 180, can be formed during a manufacturing process. For example, in one arrangement, the overdenture bar 100, support posts 140 and retention elements 180 can be machined out of a single piece of titanium such that the overdenture bar 100. It should be appreciated that some or all of the features disclosed in the various embodiments can be formed into a one-piece bar in the manufacturing process. Alternatively, the various embodiments can be formed from a multi-piece construction that is bonded together by screws, rivets, epoxy or the like. In one arrangement, the retention elements 180 can be added, removed and/or moved on the surfaces of the bar, preferably at a 90 degree angle from the surface. As illustrated in FIGS. 8 and 9, the retention elements 180 can be positioned on the top and/or side surfaces of the bar 100 and can have longitudinal centerlines that extend in a normal direction from the outer surface of the bar 100 in a plurality of directions. In other embodiments, the retention elements 180 have a longitudinal centerline that extend substantially in a normal direction wherein substantially includes within plus or minus 10 degrees or 5 degrees from the normal direction. As illustrated in the embodiment in FIG. 9, the retention elements 180 can extend in several different directions to accommodate curves in the outer surface of the bar 100. For example, in one embodiment, the bar 100 can have retention elements 180 with centerlines that extend in a generally vertical direction, a horizontal direction and/or some angle in between.

Figure 10:
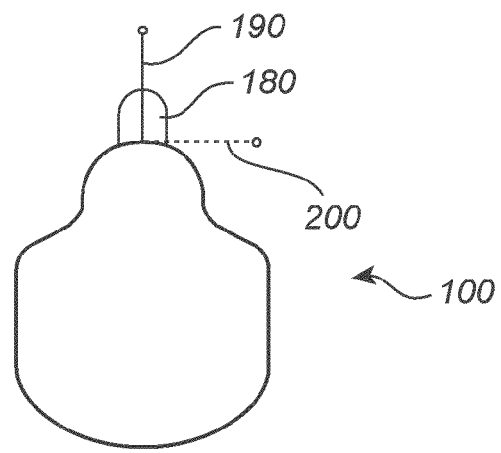
FIG. 10 illustrates a cross-sectional view of an overdenture bar as viewed on a software CAD program according to one embodiment.

FIG. 10 illustrates a cross-sectional view of an overdenture bar 100 as viewed on a software CAD program according to one embodiment. In one arrangement, the CAD software can be configured such that the user can form the retention elements 180 by clicking on an image of the surface of the bar in order to position the retention elements 180. In the illustrated arrangement in FIG. 10, each retention element 180 can be automatically oriented according to the normal surface of the bar 100 at its location. In such an arrangement, a user can select a given retention element 180 by clicking on it. Upon selecting a retention element 180, two axes 190, 200 can appear allowing the user to manipulate the size and/or shape of the retention element. The height of the retention element 180 can be manipulated by the axis 190 going through the retention element 180 (i.e. normal to the surface of the bar 100 at the retention element's 180 location). In the illustrated embodiment in FIG. 10, the height adjustment axis 190 is represented as being vertical. The width of the retention element 180 can be manipulated by the axis 200 orthogonal to the height adjustment axis 190 (i.e. tangential to the surface of the bar 100 at the retention element's 180 location). In the illustrated embodiment in FIG. 10, the width adjustment axis 200 is represented as being horizontal. It should be appreciated that the direction of the axes 190, 200 have been described by way of example only. The axes 190, 200 can be oriented in any direction on the bar 100 depending on the surface normal tangent to the bar 100 at the desired location. Further, the axes can be reversed such that the height adjustment axis 190 is tangential to the retention element 180 and the width adjustment axis 200 goes through the retention element 180. Additionally, the axes can be oriented in any two desired directions.

With further reference to FIG. 10, in another arrangement that can be used additionally or alternatively to the previously described embodiments, the user can select numerical entries (e.g., accessed through a pop up menu) to modify height and/or width dimensions of all retention elements 180 or only of one or more selected retention elements 180. In another embodiment, the user can modify the height and/or width dimensions of the retention elements 180 through the use of a single axis (e.g. by left clicking on the axis for manipulating height and right clicking on the axis for manipulating width, or by dragging the axis for manipulating height and rotating the axis for manipulating width). In another embodiment, the user can modify the height and/or width dimensions of the retention elements 180 without the use of axes (e.g. by left clicking on selected retention elements 180 for manipulating height and right clicking on selected retention elements 180 for manipulating width, or by dragging selected retention elements 180 for manipulating height and rotating selected retention elements 180 for manipulating width). In certain arrangements, the user can turn on or off the visibility of the retention elements 180. Preferably, the retention elements 180 can be seen in 2D cross-sectional views of overdenture bar 100, as well as in a 2D section of a ruler tool. In one arrangement, a retention element 180 can be removed by simply dragging the element off the image of the bar. In one arrangement, the appearance of the retention elements 180 (e.g., color or texture) can dynamically change if the retention elements 180 exceeds any design constraints. For example, in one embodiment, the color of retention elements 180 can change if the retention elements 180 are too long for the denture material such that they would interfere with the denture material.

The retention elements 180 of FIGS. 8-10 are illustrated as generally cylindrical protrusions in which the side walls and longitudinal centerline extend normal to the outer surface of the bar and wherein the top surface of the protrusions has a rounded dome shape. In modified embodiments, the retention elements 180 can have modified cross-sections and shapes and can extend at different angles from the outer surface of the bar. In one embodiment, the bar 180 can include 5 or more retention elements, and in another embodiment, 10 or more retention elements.

The above described retention elements 180 advantageously improve the retention of the wrap around denture material (e.g., acrylic) to the dental bar 100 framework. This additional support can reduce the risk of delamination, micro-movement and/or breakage of the denture material (e.g., acrylic). Another advantage of the retention elements 180 is that they can significantly enlarge the surface and/or retention area of the overdenture bar 100 without enlarging the ground structure or contact points of the bar 100 with the installed dental implants. This allows the denture material (e.g., acrylic) to have a uniform, constant and/or substantially constant thickness, which aids in aesthetics and longevity.

In the above described planning features, the CAD user can have the capability to do an optimal and virtual (CAD) design of the framework while incorporating optimal retention elements 180 for supporting the denture material (e.g., acrylic) and for the longevity of the restoration. The retention elements 180 can also simply the work in a fabrication lab by facilitating easier handling and/or easier and/or lesser manual application of the denture material (e.g., acrylic and/or composite materials) and individual layering. A further advantage of the use of retention elements 180 is the retention elements 180 can fill up volume in the overall dental restoration, which can result in the use of less denture material and therefore can reduce the cost of the denture. One advantage of incorporating the retention elements 180 in the CAD/CAM design process is improved manufacturing of the device. The retention elements 180 can be based on manufacturing and/or milling strategies that can be predefined (e.g., in "D-file" format) allowing the CAM process to be executed effectively.

Figure 11:
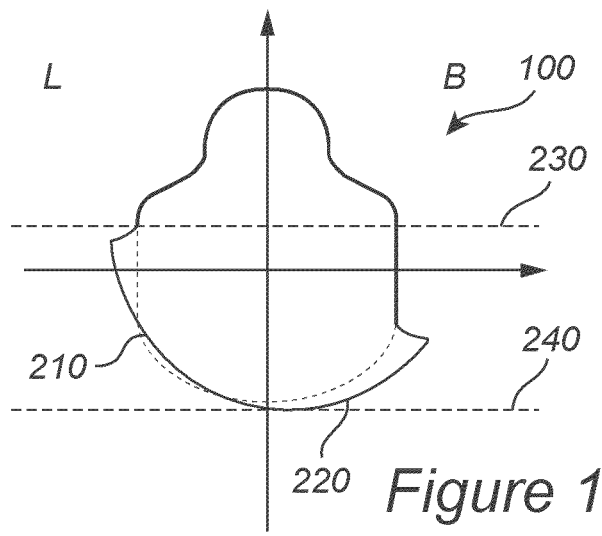
FIG. 11 illustrates a cross-sectional view of an overdenture bar as viewed on a software CAD program according to one embodiment.
Figure 12:
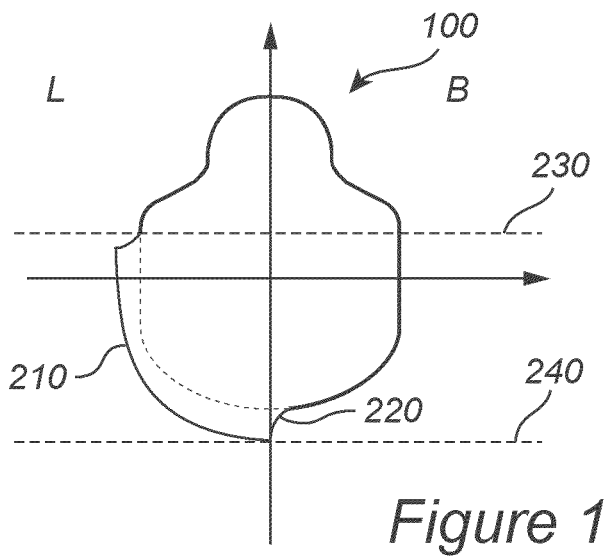
FIG. 12 illustrates a cross-sectional view of an overdenture bar as viewed on a software CAD program according to one embodiment.
Figure 13:
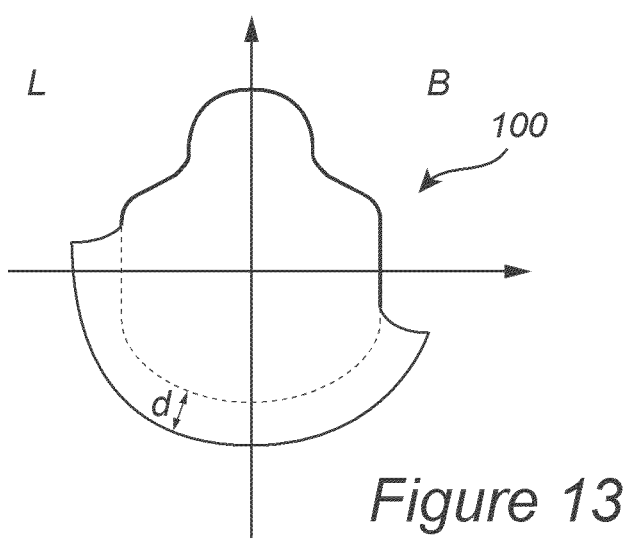
FIG. 13 illustrates a cross-sectional view of an overdenture bar as viewed on a software CAD program according to one embodiment.
Figure 14:
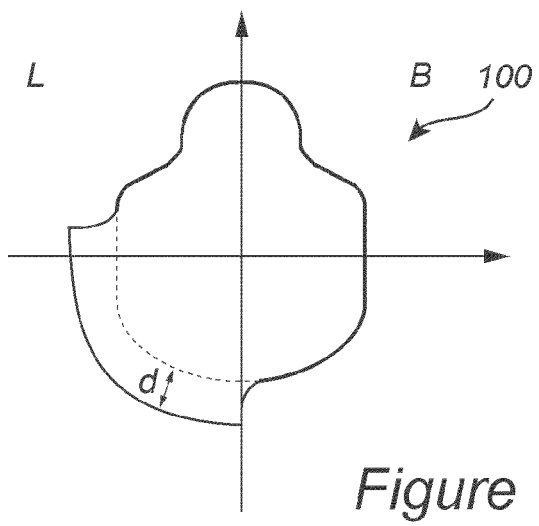
FIG. 14 illustrates a cross-sectional view of an overdenture bar as viewed on a software CAD program according to one embodiment.

FIGS. 11-16 illustrate views of overdenture bars 100 as viewed on a software CAD program according to additional and modified embodiments. With reference to FIGS. 11-15, as a separate feature or as an additional feature, the CAD software program can include an adjustment tool for lingual 210 and/or buccal 220 acrylic finish lines. For example, in one arrangement, there is the ability to add lingual 210 and/or buccal 220 acrylic finish lines similar to a Montreal bar design. In such arrangements, the bar has an exposed titanium tissue surface that can be polished to ensure sufficient hygiene. In one embodiment, the CAD user can enable or disable this feature by a checkbox included in a parameters drawer. Enabling the feature modifies the lingual 210 and buccal 220 surfaces of the bar 100 to be like a Montreal bar type as illustrated in FIG. 11. Disabling the feature restores the bar surfaces to a standard wrap-around free form bar type without an acrylic finish line.

In one arrangement, the CAD software includes manual positioning of the finish lines through handles. In one embodiment, a menu option is provided for the lingual finish line 210 and the buccal finish line 220. When this menu option is selected, handles can be enabled or disabled. The height of both finish lines can be sized to fit between the two horizontal lines 230, 240 shown in FIGS. 11 and 12. These horizontal lines illustrate the highest and lowest position of the finish lines.

With reference to the schematic FIGS. 13-16, the software CAD program can include, additionally or alternatively, features allowing the user to vary the cross-section of the overdenture bar 100 in different portions of the bar 100. For example, anterior regions 110 of the overdenture bar 100, best illustrated in FIGS. 15 and 16, can be wrapped, while posterior extensions 120 rest directly on the tissue. The CAD software can provide the ability to add lingual 210 and buccal 220 acrylic finish lines similar to the Montreal bar design and can allow the finish lines to be placed only on the posterior extensions 120 of the bar. The anterior region 110 of the bar 100 can be a wrap-around design and the posterior extensions 120 can be similar to the Montreal bar design.

Figure 15:
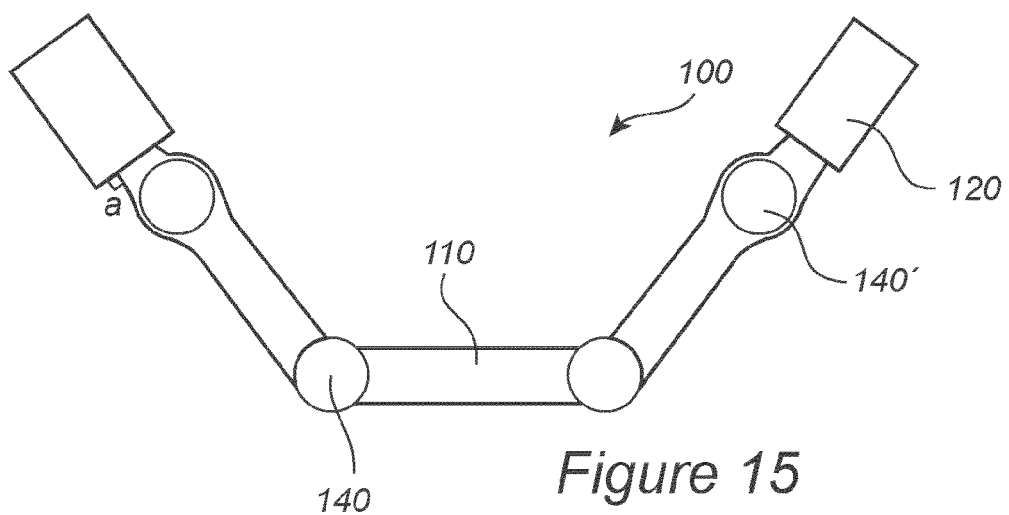
FIG. 15 illustrates a top view of an overdenture bar as viewed on a software CAD program according to one embodiment.
Figure 16:
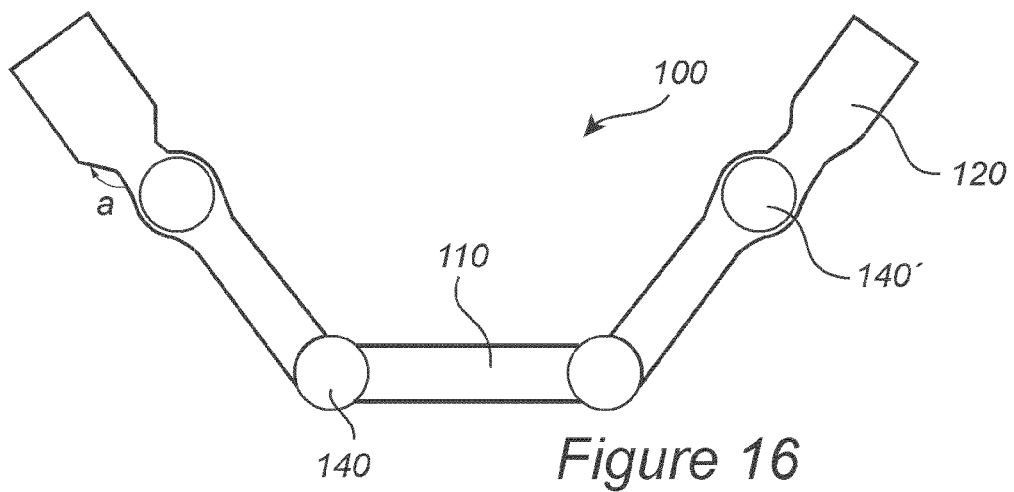
FIG. 16 illustrates a top view of an overdenture bar as viewed on a software CAD program according to one embodiment.

In one embodiment that can be used with the features described above or as a separate feature, the user can set the posterior extensions 120 as of Montreal bar type through a checkbox. The shape of the portions can be described in a "Lingual/buccal acrylic finish line adjustment tool" that consists of the shape of the wrap-around free form bar type with the lingual 210 and buccal 220 acrylic finish lines. The rest of the bar 100 can have a wrap-around free form shape. The default Montreal cross-sectional shape can be larger than the wrap-around free form shape, respecting a minimum distance everywhere on the bottom surface of the Montreal bar, in order to create a clean acrylic finish in the transition area of the two bar types. As depicted in FIGS. 15 and 16, the transition from the wrap-around free form shape to the Montreal bar shape can begin at a point beyond the most distal support post 140'. The wrap-around free form shape can join the Montreal shape with an angle a. The connection can be controlled with one or more handles in order to get a sharp or a smoother transition. To strengthen the joint between the Montreal shape and the wrap-around free form shape, lingual and/or buccal handles, which are currently available on both of these bar types, can be used. In the embodiments of schematic illustrations of FIGS. 15 and 16, the protrusions 150 described (e.g., as described above with reference to FIGS. 3A-D) can be included on these illustrated embodiments. In addition, in the embodiments of the schematic illustrations of FIGS. 3A-3D, the retention elements 180 (described above) can be included on any of the embodiments of FIGS. 15 and 16 with or without the protrusions 150.

When the design of the bar is completed, in one embodiment, the CAD/CAM file is sent to a manufacturing facility. In one embodiment, the bar can be milled machined, or otherwise formed out of a single piece of titanium. The formed bars can be shipped with either a polished shape or a non-polished shape. In one embodiment, the formed bars can have non-polished shape and the support posts can have a polished shape. Clinical screws can be packaged with the completed bar without requiring a separate order.

Figure 17:
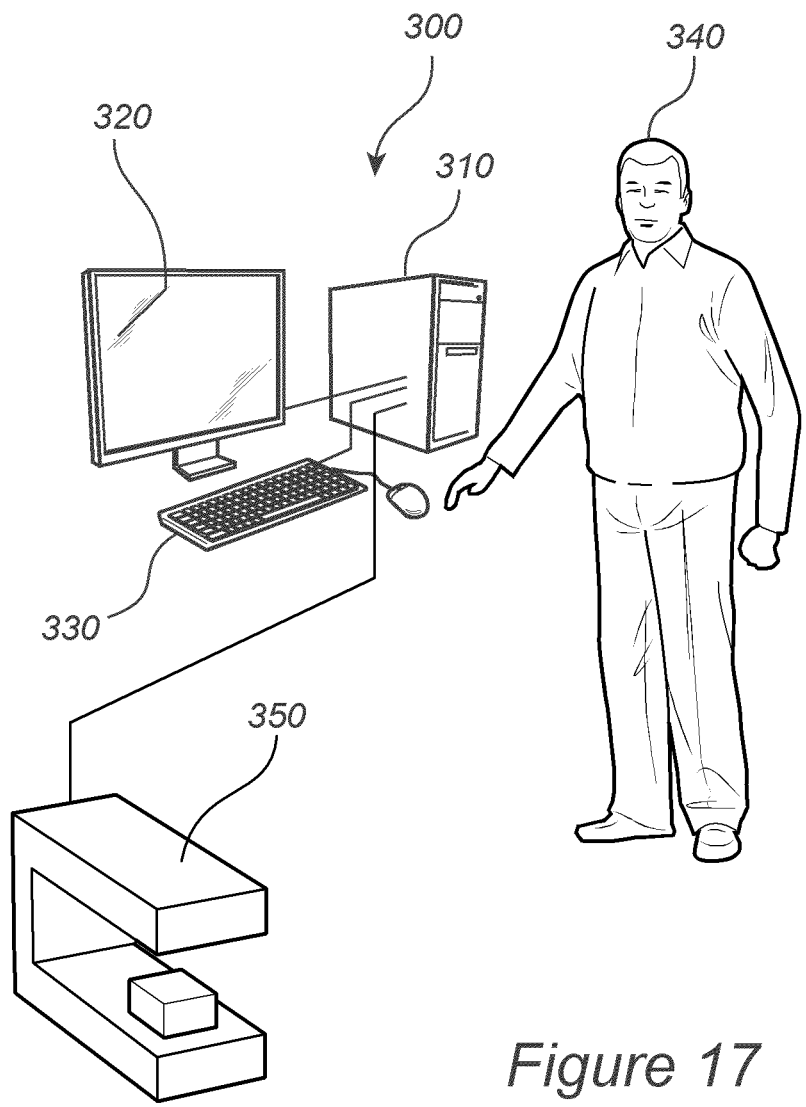
FIG. 17 illustrates an exemplary system for dental data planning according to one embodiment.

FIG. 17 illustrates an exemplary CAD system 300 for planning the overdenture bars described above. The system 300 may include one or more computers 310 coupled to one or more displays 320, one or more input devices 330 and, optionally in certain embodiments, one or more scanners 350. The one or more scanners 350 can be a 3D scanner for scanning in the model and/or denture. An operator 340, who may be a dentist, dental technician, or other person, may plan and perform the designing steps described above using the system 300 by manipulating the one or more input devices 330, which may include a keyboard and/or a mouse. In some embodiments, while working on the overdenture, the operator 340 may visualize the overdenture on the display 320. The display 320 may include two or more display regions or portions of the display, each of which displays a different aspect of the dental plan and/or overdenture. The display 320 may also have a display region allowing the operator 340 to input patient(s) data, which the operator could input using input devices 330, such as a keyboard and mouse.

In various embodiments, the computer 310 may include one or more processors, one or more memories, and/or one or more communication mechanisms. In some embodiments, more than one computer 310 may be used to execute the modules, methods, and processes discussed herein. Additionally, the modules and processes herein may each run on one or multiple processors, on one or more computers; or the modules herein may run on dedicated hardware. The input devices 330 may include one or more keyboards (one-handed or two-handed), mice, touch screens, voice commands and associated hardware, gesture recognition, or any other means of providing communication between the operator 340 and the computer 310.

The display 320 may be a 2D or 3D display and may be based on any technology, such as LCD, CRT, plasma, projection or the like. The scanner 350 may be a 2D or 3D scanner. In some embodiments, scanner 350 can accomplish 3D scanning by using time-of-flight calculations, triangulation, conoscopic holography, structured light, modulated light, computed tomography, microtomography, magnetic resonance imaging, or any appropriate technology or technique. In some embodiments, scanner 350 can accomplish 3D 3D using x-rays, visible light, laser light, ultrasound radiation, or any other appropriate radiation or technology. In some embodiments, scanner 350 can accomplish 3D scanning using stereoscopy, photometry, silhouetting, touch probe, or any other appropriate technique.

The communication among the various components of system 300 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 300 may also be combined into a single unit. In some embodiments, all of the electronic components of system 300 are included in a single physical unit.

As will be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described herein may be embodied in, and fully automated via, software code modules executed by one or more general purpose computers or processors, such as those computer systems described herein. The code modules may be stored in any type of computer-readable medium or other computer storage device. Some or all of the methods may alternatively be embodied in specialized computer hardware.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

What is claimed is:

1. A computer-implemented method for virtually designing an overdenture bar that, in use, is fitted on dental implants implanted in a patient's jawbone and supports a denture distinct from the overdenture bar, the method comprising:

displaying on a computer display a virtual model of the overdenture bar, the model comprising:

a U-shaped component displayed as a monolithic structure, wherein the U-shaped component has a cross-section defining a coronal side configured to face away from the patient's jawbone when the overdenture bar is in use, an apical side opposite from the coronal side, a standard lingual side and a standard buccal side extending between the coronal side and the apical side, the standard lingual side defining an adjustable lingual finish line and the standard buccal side defining an adjustable buccal finish line, a first post extending through the U-shaped component and comprising a first through-hole, the first post positioned based on location data of a first dental implant of the dental implants, the first post corresponding to a first member of the overdenture bar that is configured to allow the overdenture bar to be coupled to the first dental implant, and a second post extending through the U-shaped component and comprising a second through-hole, the second post positioned based on location data of a second dental implant of the dental implants, the second post corresponding to a second member of the overdenture bar that is configured to allow the overdenture bar to be coupled to the second dental implant, the first post and the second post defining therebetween an anterior region of the U-shaped component;

modifying an exterior surface of the U-shaped component, to include wave-like protrusions in the anterior region, the wave-like protrusions generally aligning with and configured to provide additional lateral support for areas of the denture that correspond to tooth structures;

adding projecting elements to the exterior surface of the U-shaped component, the projecting elements corresponding to retention elements on the overdenture bar configured to retain the denture on the overdenture bar;

adjusting the adjustable lingual finish line and/or the adjustable buccal finish line such that at least a portion of the adjustable lingual finish line extends beyond the standard lingual side and/or at least a portion of the adjustable buccal finish line extends beyond the standard buccal side;

wherein the monolithic structure of the U-shaped component remains monolithic after the steps of modifying, adding, and adjusting;

providing production data of the virtually designed overdenture bar useful for production of the overdenture bar for installing the overdenture bar on the dental implants implanted in the patient's jawbone, and wherein the method is performed programmatically by a computer-aided design system that comprises one or more physical computers.

2. The method of claim 1, wherein the U-shaped component comprises a posterior extension from the first post to a terminus of the U-shaped component distal the first post, at least some of the retention elements added in the posterior extension.

3. The method of claim 1, wherein adding the projecting elements further comprises receiving an input from clicking on a surface of the model.

4. The method of claim 1, further comprising receiving an input from selecting a menu option for specifying a dimension of at least one of the projecting elements.

5. The method of claim 1, further comprising displaying on the computer display a model of a wrap around denture for the overdenture bar.

adjusting the adjustable lingual finish line such that at least a portion of the adjustable lingual finish line extends beyond the standard lingual side, and adjusting the adjustable apical finish line such that at least a portion of the adjustable apical finish line extends beyond the apical side.

6. The method of claim 1, wherein the step of adjusting comprises adjusting the adjustable lingual finish line such that at least a portion of the adjustable lingual finish line extends beyond the standard lingual side.

7. The method of claim 1, wherein the step of adjusting comprises adjusting the adjustable buccal finish line such that at least a portion of the adjustable buccal finish line extends beyond the standard buccal side.

8. The method of claim 1, wherein the step of adjusting comprises adjusting the adjustable lingual finish line such that at least a portion of the adjustable lingual finish line extends beyond the standard lingual side, and adjusting the adjustable buccal finish line such that at least a portion of the adjustable buccal finish line extends beyond the standard buccal side.

9. The method of claim 1, wherein the apical side of the U-shaped component further defines an adjustable apical finish line and the step of adjusting comprises adjusting the adjustable lingual finish line such that at least a portion of the adjustable lingual finish line extends beyond the standard lingual side, and adjusting the adjustable apical finish line such that at least a portion of the adjustable apical finish line extends beyond the apical side.

10. The method of claim 1, wherein the retention elements have straight sides normal to the overdenture bar.

11. The method of claim 1, wherein the retention elements extend in a substantially normal direction from an outer surface of the U-shaped component in a plurality of directions.

12. The method of claim 1, additionally comprising defining radii of a curved lingual bottom edge and buccal bottom edge of the cross-section of the U-shaped component.

13. The method of claim 1, wherein the production data defines an overdenture bar, including the first post, the second post, the wave-like protrusions and the projecting elements, to be manufactured from a single piece of material.

14. The method of claim 1, wherein the adjustable lingual finish line and/or the adjustable buccal finish line are limited to being adjusted between a particular upper finish line boundary and a particular lower finish line boundary.

15. The method of claim 2, wherein adjusting the adjustable lingual finish line and/or the adjustable buccal finish line is limited to being adjusted in the posterior extension.

16. The method of claim 15, wherein a transition between the anterior region without the adjusted lingual finish line and/or the adjusted buccal finish line and the posterior extension having the adjusted lingual finish line and/or the adjusted buccal finish line is controlled to have a particular angle for the transition.

17. A computer-implemented method for virtually designing an overdenture bar that, in use, is fitted on dental implants implanted in a patient's jawbone and supports a denture distinct from the overdenture bar, the method comprising:

displaying on a computer display a virtual model of the overdenture bar, the model comprising a U-shaped component displayed as a monolithic structure, wherein the U-shaped component has a cross-section defining a coronal side configured to face away from the patient's jawbone when the overdenture bar is in use, an apical side opposite from the coronal side, a standard lingual side and a standard buccal side extending between the coronal side and the apical side, the standard lingual side defining an adjustable lingual finish line and the standard buccal side defining an adjustable buccal finish line;

modifying an exterior surface of the U-shaped component to include wave-like protrusions generally aligning with and configured to provide additional lateral support for areas of the denture that correspond to tooth structures;

adjusting the adjustable lingual finish line and/or the adjustable buccal finish line such that at least a portion of the adjustable lingual finish line extends beyond the standard lingual side and/or at least a portion of the adjustable buccal finish line extends beyond the standard buccal side, wherein the monolithic structure of the U-shaped component remains monolithic after the steps of modifying and adjusting;

providing production data of the virtually designed overdenture bar useful for production of the overdenture bar for installing the overdenture bar on the dental implants implanted in the patient's jawbone, and wherein the method is performed programmatically by a computer-aided design system that comprises one or more physical computers.

18. The method of claim 17, further comprising displaying on the computer display a model of a wrap around denture for the overdenture bar.

19. The method of claim 17, wherein the step of adjusting comprises adjusting the adjustable lingual finish line such that at least a portion of the adjustable lingual finish line extends beyond the standard lingual side.

20. The method of claim 17, wherein the step of adjusting comprises adjusting the adjustable buccal finish line such that at least a portion of the adjustable buccal finish line extends beyond the standard buccal side.

21. The method of claim 17, wherein the step of adjusting comprises
adjusting the adjustable lingual finish line such that at least a portion of the adjustable lingual finish line extends beyond the standard lingual side, and
adjusting the adjustable buccal finish line such that at least a portion of the adjustable buccal finish line extends beyond the standard buccal side.

22. The method of claim 17, wherein the apical side of the U-shaped component further defines an adjustable apical finish line and the step of adjusting comprises
adjusting the adjustable lingual finish line such that at least a portion of the adjustable lingual finish line extends beyond the standard lingual side, and
adjusting the adjustable apical finish line such that at least a portion of the adjustable apical finish line extends beyond the apical side.

23. A computer-implemented method for virtually designing an overdenture bar that, in use, is fitted on dental implants implanted in a patient's jawbone and supports a denture distinct from the overdenture bar, the method comprising:
displaying on a computer display a virtual model of the overdenture bar, the model comprising a U-shaped component displayed as a monolithic structure, wherein the U-shaped component has a cross-section defining a coronal side configured to face away from the patient's jawbone when the overdenture bar is in use and an apical side opposite from the coronal side, the apical side defining an adjustable finish line;
modifying an exterior surface of the U-shaped component in an anterior region to include wave-like protrusions generally aligning with and configured to provide additional lateral support for areas of the denture that correspond to tooth structures; and
adjusting the adjustable finish line such that at least a portion of the adjustable finish line extends beyond the apical side,
wherein the monolithic structure of the U-shaped component remains monolithic after the steps of modifying and adjusting;
providing production data of the virtually designed overdenture bar useful for production of the overdenture bar for installing the overdenture bar on the dental implants implanted in the patient's jawbone, and
wherein the method is performed programmatically by a computer-aided design system that comprises one or more physical computers.

* * * * *

UNITED STATES PATENT AND TRADEMARK OFFICE
CERTIFICATE OF CORRECTION

PATENT NO. : 10,383,709 B2
APPLICATION NO. : 13/799691
DATED : August 20, 2019
INVENTOR(S) : David Giasson Page 1 of 1

It is certified that error appears in the above-identified patent and that said Letters Patent is hereby corrected as shown below:

In the Claims

Column 13, Lines 43-48, in Claim 5, below "bar." delete "adjusting the adjustable lingual finish line such that at least a portion of the adjustable lingual finish line extends beyond the standard lingual side, and adjusting the adjustable apical finish line such that at least a portion of the adjustable apical finish line extends beyond the apical side.".

Signed and Sealed this
Thirty-first Day of December, 2019

Andrei Iancu
*Director of the United States Patent and Trademark Office*